United States Patent [19]

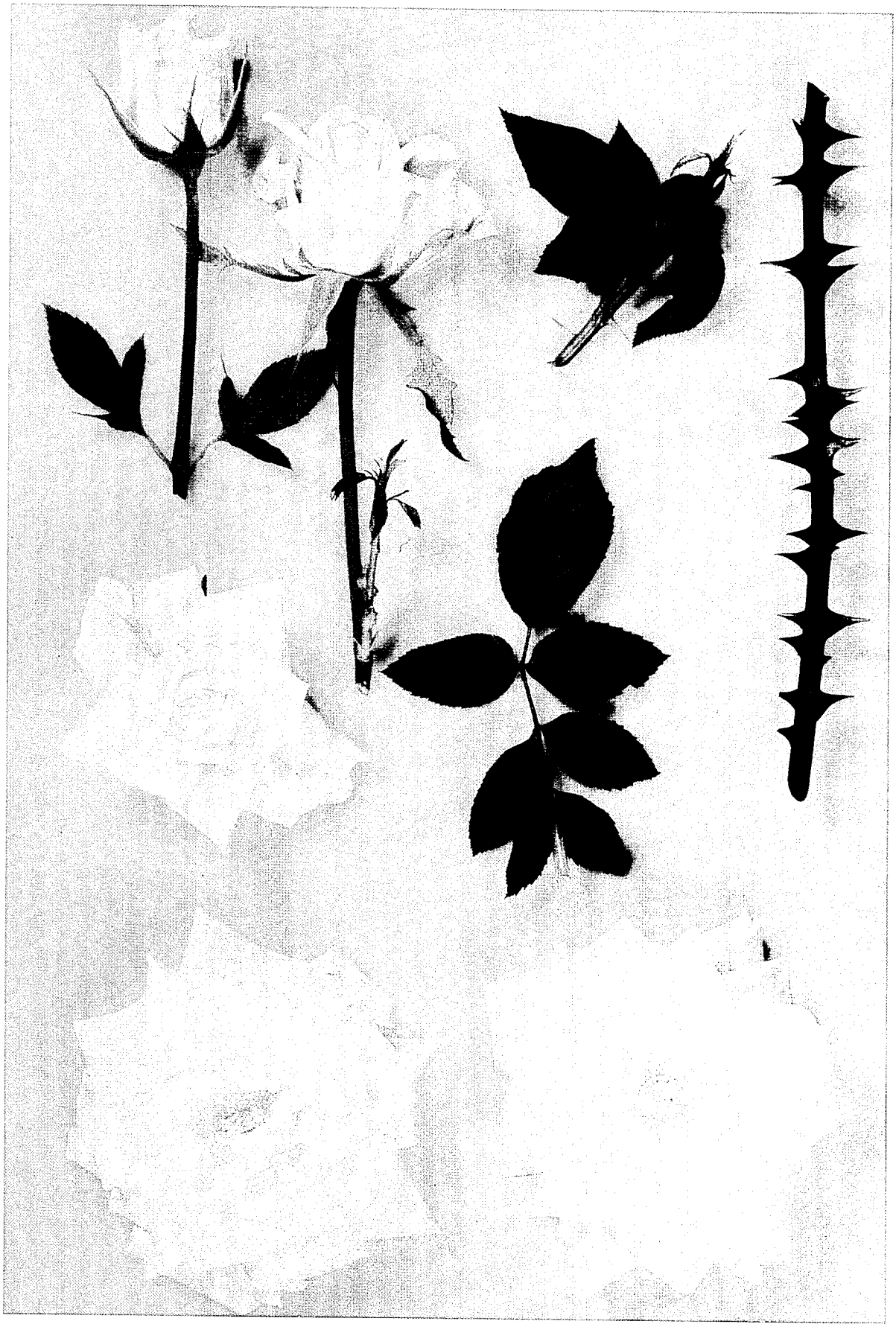

Warriner

[11] Plant 4,438

[45] Jul. 17, 1979

[54] ROSE PLANT

[75] Inventor: William A. Warriner, Tustin, Calif.

[73] Assignee: Jackson & Perkins Co., Medford, Oreg.

[21] Appl. No.: 892,482

[22] Filed: Mar. 31, 1978

[51] Int. Cl.[2] ..... A01H 5/00

[52] U.S. Cl. ..... Plt./15

[58] Field of Search ..... Plt./15

*Primary Examiner*—Robert E. Bagwill

*Attorney, Agent, or Firm*—Klarquist, Sparkman, Campbell, Leigh, Hall & Whinston

[57] ABSTRACT

A vigorous, upright, branching rose plant of the hybrid tea class, having chrome yellow color of buds and blooms, stems with numerous, long straight prickles, little fragrance, and good resistance to rose powdery mildew.

8 Drawing Figures

1

ROSE PLANT — SUNBRIGHT

The present invention relates to a new and distinct variety of rose plant of the hybrid tea class which was originated by me by crossing an unnamed, unreleased variety with pollen of the variety New Day, U.S. Plant Pat. No. 3,228.

The primary objective of this breeding was to produce a new rose variety of the hybrid tea class having growth characteristics similar to those of New Day and with a flower color which is yellow without the fading sometimes occurring on New Day. This objective was substantially achieved along with other desirable improvements as evidenced by the following unique combination of characteristics which are outstanding in the new variety and which distinguish it from its parents as well as from all other varieties of which I am aware:

1. A vigorous, heavily branched habit of growth.
2. Buds and flowers produced in a greenhouse have a uniform color of Chrome Yellow (Wilson) with very little or no change from the bud stage to fully open stage.
3. Good resistance to rose powdery mildew.
4. Stems with numerous straight, long prickles.
5. Very little fragrance.

Asexual reproduction of this new cultivar by budding as performed at Wasco, Calif., shows that the foregoing characteristics and distinctions come true to form and are established and transmitted through succeeding propagations.

The accompanying illustration shows typical specimens of the vegetative growth and flowers of this new cultivar in different stages of development, depicted in color as nearly true as it is reasonably possible to make the same in a color illustration of this character.

The following is a detailed description of my new rose cultivar with color in terminology in accordance with Wilson's Horticultural Color Chart, except where ordinary dictionary significance of color is indicated.

Parentage:

*Seed parent.*—Unnamed Cultivar.

*Pollen parent.*—New Day, U.S. Plant Pat. No. 3,228.

Classification:

*Botanical.*—Rosa hybrid.

*Commercial.*—Hybrid tea.

2

FLOWER

Observations made from specimens grown in the greenhouse and in the garden at Irvine, Calif., in December 1977.

Blooming Habit: Continuous.

Bud:

*Size.*—Approximately from 1.25 to 1.5 inches when petals start to unfurl.

*Form.*—Long, pointed ovoid.

*Color.*—When sepals first divide, Chrome Yellow (605/1); when half blown; upper side of petals Chrome Yellow (605/5); lower side of petals Chrome Yellow (605/1).

*Sepals.*—Color: Outer surface Scheeles Green (860/3); inner surface Scheeles Green (860/3). Three appendaged sepals, heavily appendaged. Two unappendaged sepals, hairy edged.

*Receptacle.*—Color: Scheeles Green (860/3). Shape: Funnel. Size: Small. Surface: Smooth.

*Peduncle.*—Length: Medium. Surface: Smooth. Color: Light green. Strength: Stiff, erect.

*Opening.*—Petals curl back, become slightly pointed when fully open.

Bloom:

*Size.*—Large. Average open size 4.5 to 5 inches.

*Borne.*—Singly, and several together.

*Stems.*—Medium.

*Form.*—When first open — high centered. Permanence — flattens when fully opened.

*Petalage.*—Number of petals under normal conditions — 25 to 35.

*Color.*—Center of flower: Upper side of petals Chrome Yellow (605/1). Reverse side of petals Chrome Yellow (605/2). Base of petals Chrome Yellow (605/1). General tonality from a distance Chrome Yellow (605/1).

*Variegations.*—Occasional vegetative green midrib areas on outer petals.

*Discoloration.*—General tonality at end of first day: Chrome Yellow (605/1); third day: Chrome Yellow (605/1).

*Fragrance.*—Slight to none.

Petals:

*Texture.*—Thin.

*Shape.*—Round.

*Form.*—Edges slightly quilled.

*Arrangement.*—Imbricated. Petaloids few.
*Persistence.*—Drop off cleanly.
*Lastingness.*—On the plant, long. As cut flower, long.

Reproductive parts:
*Stamens, anthers.*—Medium, many. Color, yellow. Arrangement, regular around styles.
*Filaments.*—Color, Lemon Yellow (4).
*Pollen.*—Gold yellow.
*Styles.*—Color: Chartreuse Green (663/1) with pink markings below stigmas.
*Stigmas.*—Color: yellow.

PLANT

Form: Bush.
Growth: Very vigorous, upright, branching.
Foliage: Number of leaflets on normal mid-stem leaves: 5 or 7.
*Size.*—Medium.
*Quantity.*—Abundant.
*Color.*—New foliage: lighter than Garnette Brown (00918/3) changing quickly to its mature stage color of Spinach Green (0960/3).

Leaflets:
*Shape.*—Oval pointed.
*Texture.*—Leathery.

*Edge.*—Serrated.
*Serration.*—Single, small.
*Petiole.*—Rachis: Color, green. Underside: prickly.
*Stipules.*—Long, bearded.
*Disease resistance.*—Resistant to mildew under normal growing conditions at Irvine, Calif.

Wood:
*New wood.*—Color: Light green. Bark: Smooth.
*Old wood.*—Color: Green. Bark: Smooth.

Prickles:
*Quantity.*—On main stalks from base, many. On laterals from stalk, many.
*Form.*—Narrow base, long, straight.
*Color when young.*—Light Green.
*Position.*—Irregular.

Small prickles:
*Quantity.*—On main stalks, none.

I claim:

1. A new and distinct variety of rose plant of the hybrid tea class, substantially as herein shown and described, characterized particularly as to novelty by the unique combination of its heavily branched plant, Chrome Yellow color of buds and blooms, good resistance to rose powdery mildew, lack of fragrance and stems with numerous, long straight prickles.

* * * * *

UNITED STATES PATENT AND TRADEMARK OFFICE

CERTIFICATE OF CORRECTION

PATENT NO. : Plant 4438

DATED : July 17, 1979

INVENTOR(S) : William A. Warriner

It is certified that error appears in the above–identified patent and that said Letters Patent are hereby corrected as shown below:

Column 2, line 14, "(605/5)" should be --(605/1)--.

Signed and Sealed this

*Twenty-second* Day of *January 1980*

[SEAL]

*Attest:*

SIDNEY A. DIAMOND

*Attesting Officer*

*Commissioner of Patents and Trademarks*